United States Patent [19]
Ito et al.

[11] Patent Number: 5,427,087
[45] Date of Patent: Jun. 27, 1995

[54] STRUCTURE OF THE DISTAL END PORTION OF AN ENDOSCOPE

[75] Inventors: Keiji Ito; Hiroshi Iwata, both of Tokyo, Japan

[73] Assignee: Asahi Kogaku Kogyo Kabushiki Kaisha, Tokyo, Japan

[21] Appl. No.: 797,975

[22] Filed: Nov. 26, 1991

[30] Foreign Application Priority Data

Nov. 26, 1990 [JP] Japan ................... 2-321418

[51] Int. Cl.$^6$ ............................... A61B 1/04
[52] U.S. Cl. ................................ 128/4; 128/6
[58] Field of Search ............ 128/4, 6, 7, 8, 11, 128/13; 358/98; 385/36, 116, 117, 119; 359/831, 833, 836

[56] References Cited

U.S. PATENT DOCUMENTS

| | | | |
|---|---|---|---|
| 4,741,327 | 5/1988 | Yabe | 128/6 |
| 4,832,003 | 5/1989 | Yabe | 128/6 |
| 4,895,138 | 1/1990 | Yabe | 128/6 |

*Primary Examiner*—Richard J. Apley
*Assistant Examiner*—John P. Leubecker
*Attorney, Agent, or Firm*—Sughrue, Mion, Zinn, Macpeak & Seas

[57] ABSTRACT

The distal end body of an endoscope accommodates an objective optical system, and a solid-state image pick-up element having a light receiving surface is disposed axially in parallel with the center axis of the objective optical system. A prism is disposed such that the optical axis of the objective optical system is perpendicular to the center axis of the light receiving surface. An object is imaged on the light receiving surface of the solid-state image pick-up element, through the objective optical system. The prism is shaped like a trapezoid in cross-section to minimize the size of the endoscope.

6 Claims, 5 Drawing Sheets

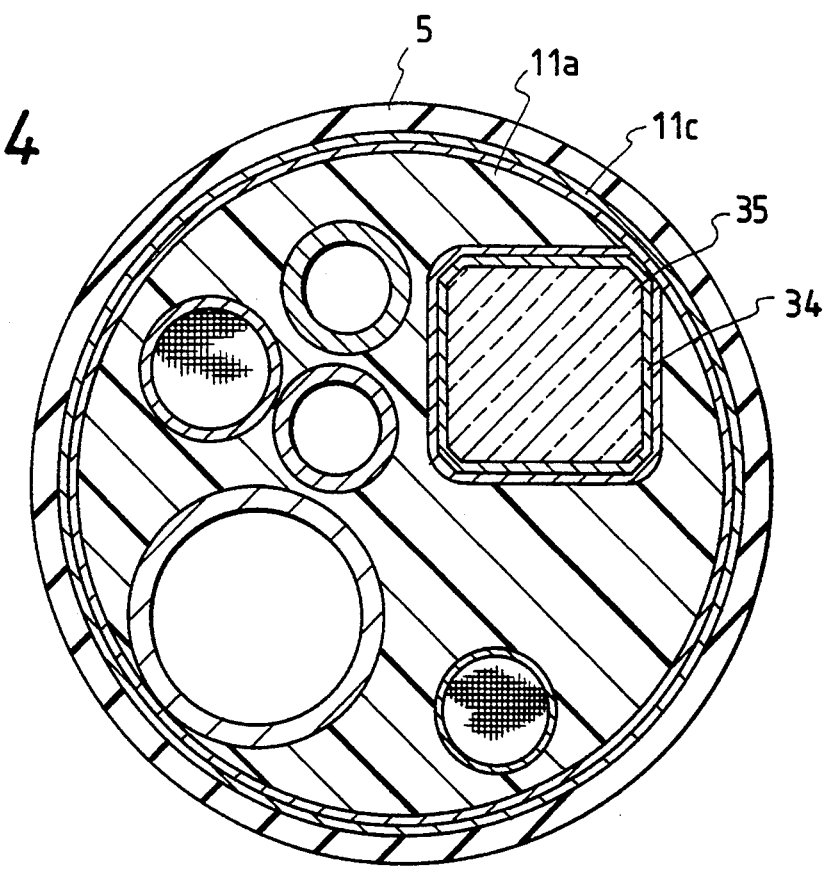
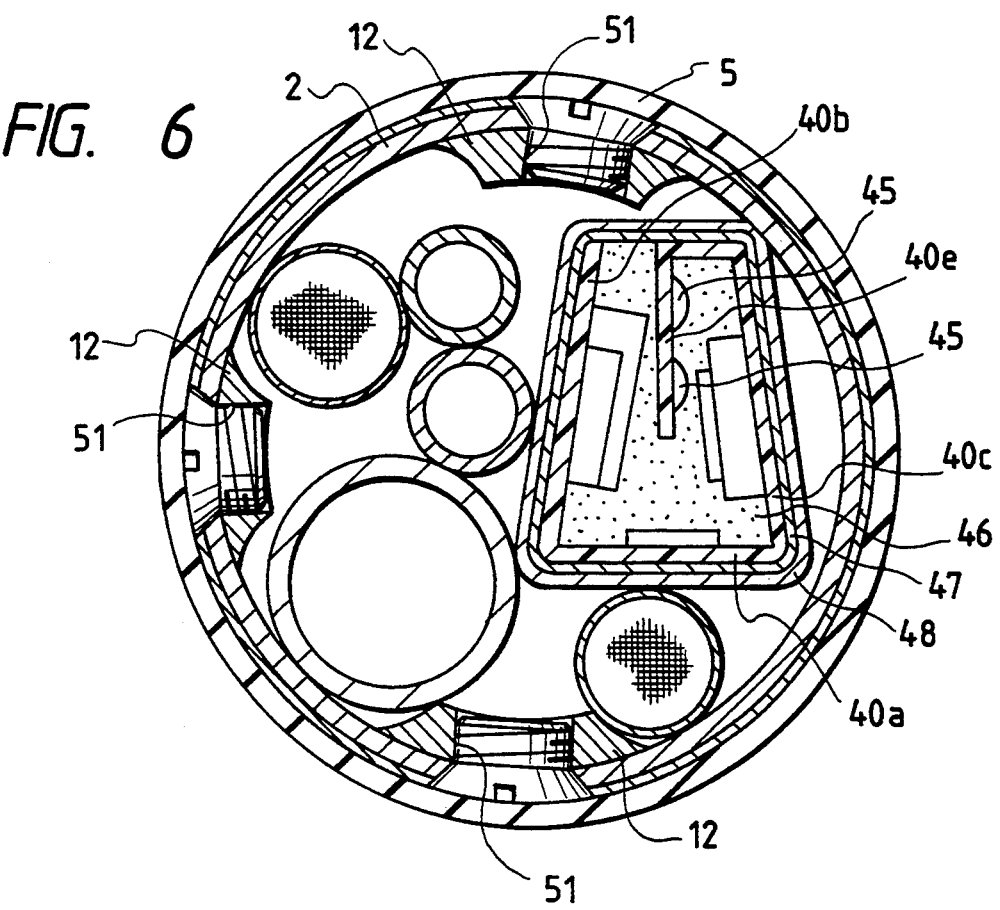

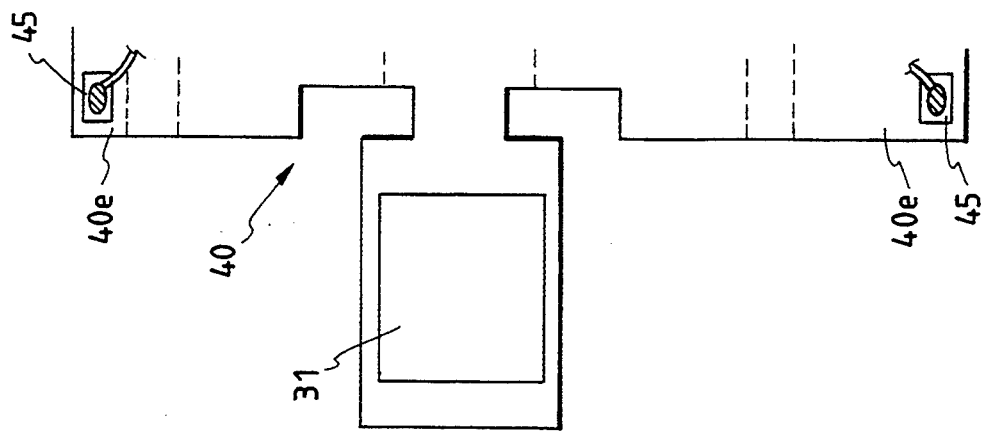
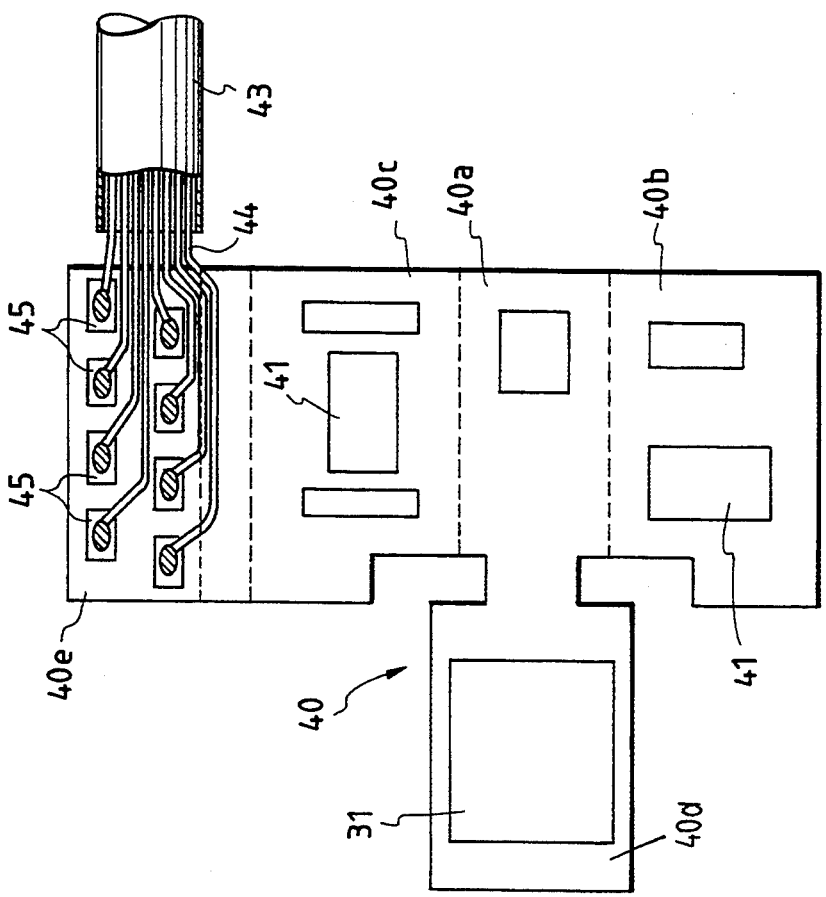

STRUCTURE OF THE DISTAL END PORTION OF AN ENDOSCOPE

BACKGROUND OF THE INVENTION

This application is based on, and claims priority from, Japanese Application No. HEI 2-321418 filed Nov. 26, 1990, the disclosure of which is incorporated herein by reference.

The present invention relates to the distal end portion of an endoscope of the type in which a prism for bending an optical path at a substantially right angle is disposed between an objective optical system and a solid-state image pick-up element.

It is known to utilize an endoscope in which the light receiving surface of a solid-state image pick-up element is oriented in parallel with the center axis of an objective optical system so that it does not occupy too much of the cross sectional area of the interior of the distal end of the endoscope.

FIG. 8A is a schematic illustration showing the distal end 100 of this type of conventional endoscope. As shown, the optical axis of objective optical system 101 is bent by rectangular prism 102 and reaches light receiving surface 103a of a solid-state image pick-up element 103. The shape of rectangular prism 102 is rectangular or square in cross-section when viewed from objective optical system 101, as shown in FIG. 8B.

Prism 102 thus occupies a large proportion of the cross sectional area of distal end 100 of the endoscope. Within distal end 100, the members to be contained, such as a fluid pipe and a light guide fiber bundle, are disposed in the remaining space. The result is an increase in the diameter of distal end 100 of the endoscope. If distal end 100 is of a large diameter, insertion may be difficult and uncomfortable for the patient.

SUMMARY OF THE INVENTION

The present invention has been made in view of the above circumstances, and it is an object of the invention to provide an arrangement for the distal end portion of an endoscope which permits a smaller diameter of the distal end.

To achieve the above object, the invention comprises an endoscope having a distal end portion accommodating an objective optical system and a solid-state image pick-up element, with the pick-up element having a light receiving surface disposed in parallel with the center axis of the objective optical system, and a prism disposed between the objective optical system and the light receiving surface of the solid-state image pick-up element. An object is imaged on the light receiving surface of the solid-state image pick-up element, through the objective optical system and the prism. The prism is shaped like a trapezoid in cross-section as viewed from the objective optical system. The trapezoidal shape of the prism minimizes the area occupied by the prism in the distal end portion.

Also, in the distal end portion of an endoscope according to the invention, a circuit board connected to the solid-state image pick-up element may be disposed within the distal end body in a state that it closely tracks the outer edge of the prism when viewed from the objective optical system. Therefore, the presence of the circuit board within the distal end portion will not substantially increase the diameter of the distal end portion, and a smooth insertion of the distal end portion into the body cavity is ensured.

The circuit board may consist of a plurality of planar surfaces folded so as to form a trapezoid in cross section. One of the planar surfaces which is on one side of the circuit board having terminals disposed thereon may be bent downward at the center of the upper shorter side of the trapezoid. If two cables are used, the terminals to which lead wires of the cables are soldered respectively, may be formed on both sides of the circuit board.

BRIEF DESCRIPTION OF THE DRAWINGS

The invention will be more clearly understood with reference to the following description in conjunction with the accompanying drawings, wherein:

FIG. 4 is a cross sectional view taken on line IV—IV in FIG. 2;

FIG. 5 is a circuit board used in the embodiment of FIG. 2;

FIG. 6 is a cross sectional view taken on line VI—VI in FIG. 2;

FIG. 7 is a different circuit board which can be used in the embodiment of FIG. 2;

DETAILED DESCRIPTION OF THE PREFERRED EMBODIMENT

The preferred embodiment of the invention will now be described in detail with reference to the accompanying drawings.

Figure 2:
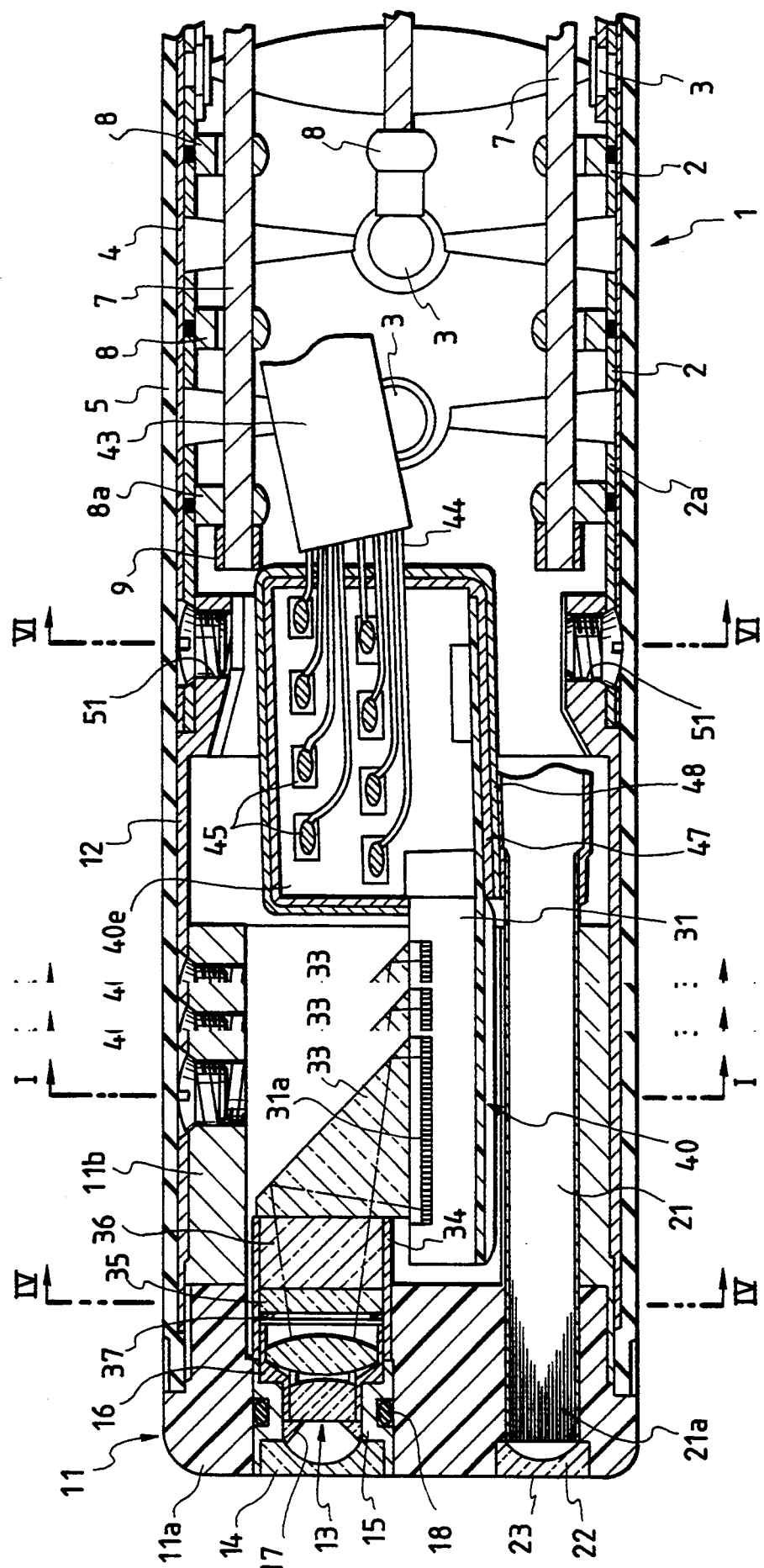
FIG. 2 is a longitudinal sectional view showing the structure of the distal end portion of an endoscope according to an embodiment of the present invention.
Figure 8B:
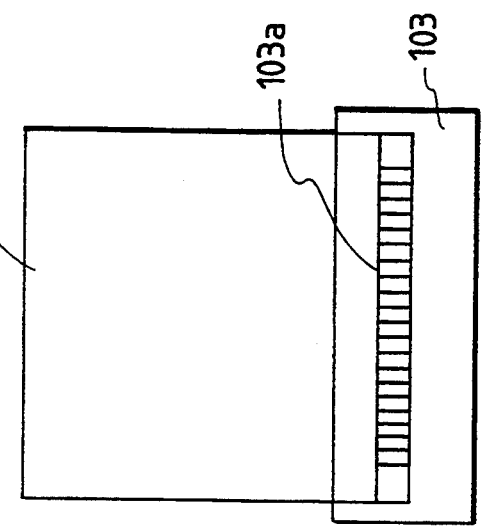
FIG. 8B is a view of a prism assembled into the structure of the conventional distal end portion of an endoscope as viewed from the objective optical system of the endoscope.
Figure 8A:
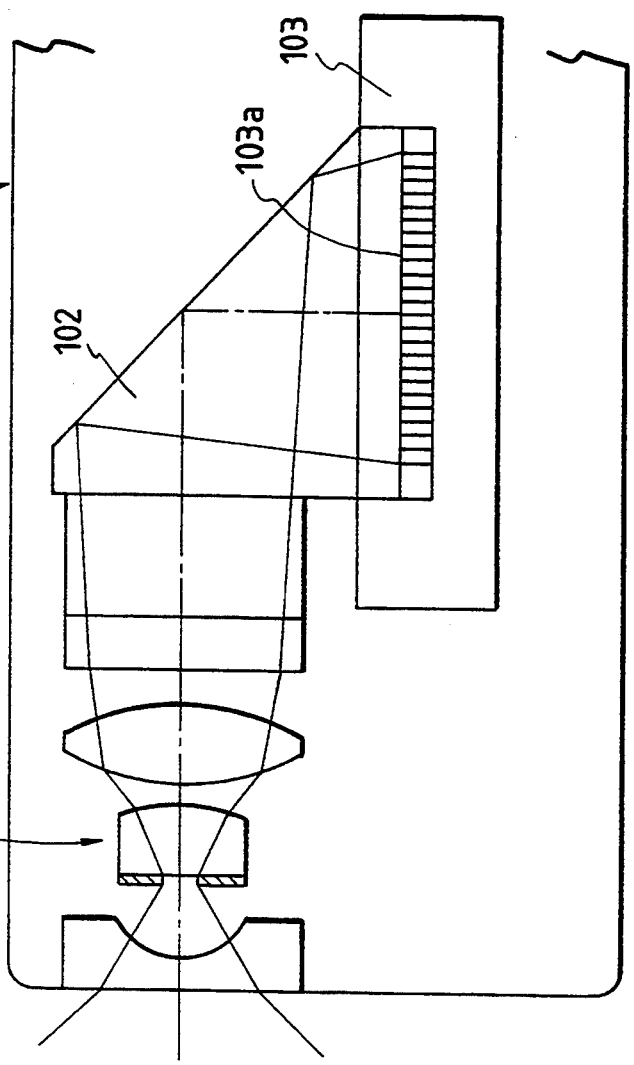
FIG. 8A is a schematic diagram showing the distal end portion of a conventional endoscope.

FIG. 2 is a longitudinal sectional view showing the structure of the distal end portion of an endoscope according to an embodiment of the present invention. Bendable portion 1 is at the distal end of a slender, flexible pipe which serves as an insertion portion of the endoscope. In bendable portion 1, a plurality of nodal rings 2 are rotatably coupled with each other by means of rivets 3. Nodal rings 2 are covered with mesh tube 4 made of fine metal wires and sheathing tube 5 made of rubber.

Bendable operating wires 7, capable of being manipulated remotely, are retractably placed within wire guides 8 which extend inwardly from nodal rings 2 respectively. The tip of bendable operating wires 7 are fixed to wire guide 8a which is provided in nodal ring 2a closest to the distal end of the insertion portion by silver brazing. Stopper pipe 9 is fixed to the end of wire guide 8a by silver brazing so as to prevent operating wire 7 from slipping off of wire guide 8a. Distal end body 11 is coupled with the tip of bendable portion 1 by means of coupling tube 12. Distal end body 11 is formed with metal body part 11b and head part 11a, made of electrically insulating plastic, which is coupled with the distal side of the metal body part 11b. Distal end body 11 is, of course, circular in cross section when seen from the distal end (the left side in FIG. 2).

Objective optical system 13 is contained within the head part 11a and consists of a plurality of lenses, its axis is parallel to that of distal end body 11. Light from an observed object is made incident to the incident side surface of the objective optical system (the left side in FIG. 2). A view window 14 consists of the foremost lens of the objective optical system 13.

Lens barrel 15 and 16 are provided by which the respective lenses of objective optical system 13 are fixedly held. Lens barrel 15 is bonded to head part 11a of distal end body 11. Aperture diaphragm 17 is provided in behind of view window 14, and O-ring 18 is provided for sealing purposes between head part 11a and lens barrel 15.

Light emitting end 21a of light guide fiber bundle 21 is secured to head part 11a of distal end body 11, while having an axis that is parallel with objective optical system 13. Concave lens 22, for dispersing the illumination light emitted, is disposed on the distal end face of light emitting end 21a and forms an illumination window. Illumination light transmitted through light guide fiber bundle 21 illuminates objects located ahead of distal end body 11.

Figure 3:
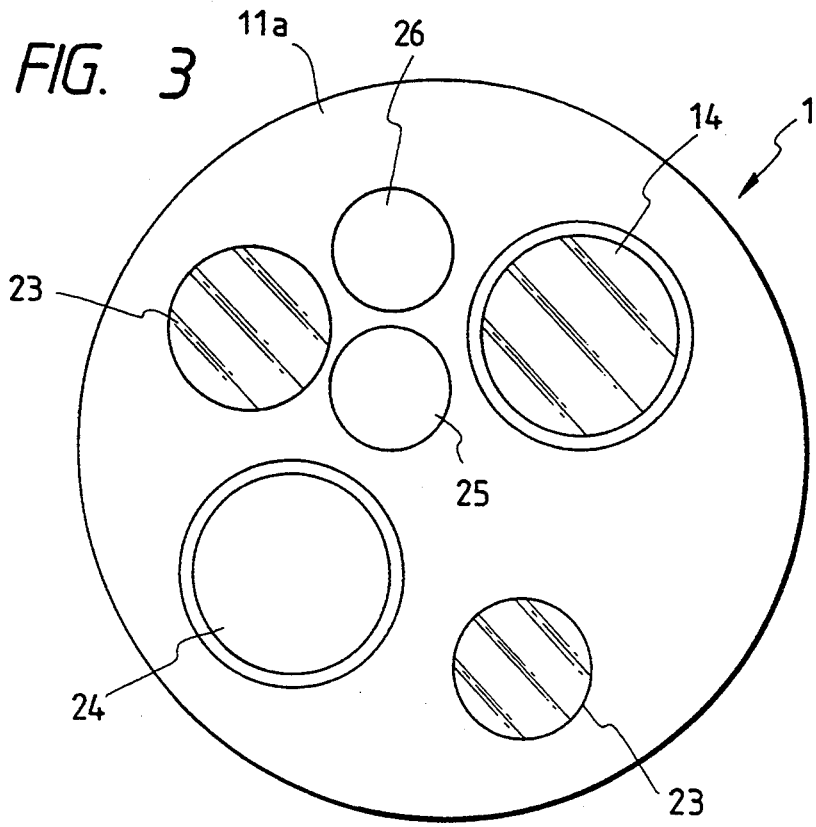
FIG. 3 is a front view showing the endoscope of FIG. 2.

FIG. 3 is a front view showing head part 11a of distal end body 11. As illustrated, two illumination windows 23 are provided, and an associated light guide fiber bundle 21 is behind each window 23. Port 24 is provided for the passage of surgical instruments, such as forceps, or the like and for suction. Air-feed nozzle 25 and Water-feed nozzle 26 are also provided to clean the surface of the view window.

Returning to FIG. 2, solid-state image pick-up element 31 is disposed within body part 11b. Solid-state image pick-up element 31 may be a CCD (charge coupled diode), or the like. Light receiving surface 31a of solid-state image pick-up element 31 is rectangular or square, and disposed in parallel with the center axis of objective optical system 13.

Prism 33 is disposed between the objective optical system 13 and the solid-state image pick-up element 31. Prism 33 is disposed to direct light traveling through objective optical system 13 onto light receiving surface 31a.

Optical coupling tube 34 coupled with lens barrel 16, has flare mask 37, color correction filter 35, and low-pass filter 36 contained therein and is disposed between rectangular prism 33 and objective optical system 13. With such a structure, an object (not shown) located on the left side of view window 14 in FIG. 2 is imaged on light receiving surface 31a of solid-state image pick-up element 31, through objective optical system 13 and prism 33. As shown in FIG. 4, coupling tube 34 and the optical elements disposed therewithin are shaped to be substantially square in cross section, with the four corners, which are unnecessary to transmit the light beam cut off.

Figure 1:
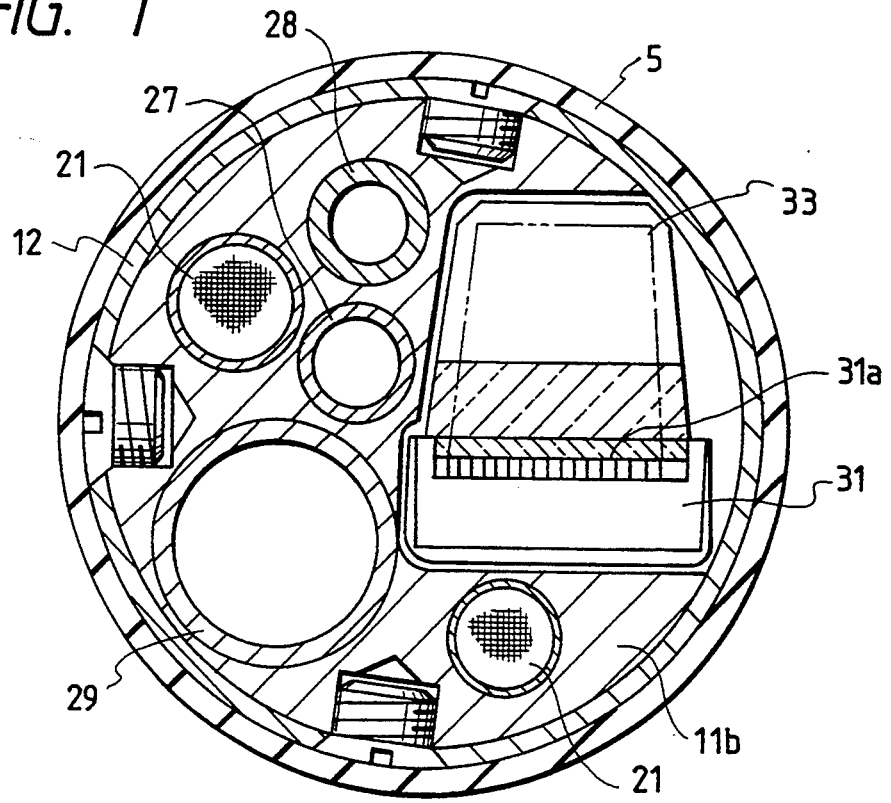
FIG. 1 is a cross sectional view taken on line I—I in FIG. 2.

In this embodiment, objective optical system 13 is designed such that a principal ray traveling from the observed object through objective optical system 3 to solid-state image pick-up element 31 gradually diverges as indicated by one-dot-chain lines in FIG. 2. Solid-state image pick-up element 31, unlike a conventional light guide fiber bundle, is capable of receiving light with relatively low loss even if the light is obliquely incident thereon. It is for this reason that objective optical system 13 can be of a type in which a principal ray diverges. Due to the use of the objective optical system 13, the outer configuration of light passing through prism 33 gradually diverges as the light approaches high receiving surface 31a, as indicated by a two-dot-chain line in FIG. 1.

Prism 33 is shaped like a trapezoid in cross section, with non-parallel sides gradually diverging toward light receiving surface 31a, i.e., it is substantially parallel to the outer configuration of light passing therethrough. The shape of prism 33 minimizes the area occupied thereby in the cross sectional area of distal end body 11. Accordingly, it allows distal end body 11 to be small in cross section.

Air-feed pipe 27 and water-feed pipe 28 are also provided along the length of distal end body 11 the endoscope (see FIG. 1), which are connected to nozzles 25, 26, respectively. In addition, surgical instrument insertion pipe 29, for the insertion of forceps or other surgical instruments and for suction, is provided, which opens to outside at the distal end through port 24.

Circuit board 40, on which solid-state image pick-up element 31 is mounted, consists of a flexible, electrically insulating plastic plate, as shown in FIG. 5. Circuit board 40 is divided into five planar surfaces. The five planar surfaces 40a–40e are folded along broken lines which extend in the axial direction of distal end body 11 (see FIGS. 2 and 6). Electronic circuits are formed on planar surfaces 40b and 40c, which are on each side of planar surface 40a having solid-state image pick-up element 31 mounted thereon. Various types of electronic parts 41 may be mounted on planar surfaces 40b and 40c. Terminals 45 which are electrically connected to electronic circuits board 40 are formed on uppermost planar surface 40e. Lead wires 44 of cable 43, which are inserted into bendable portion 1 from the flexible tube of the endoscope, are soldered to terminals 45.

Circuit board 40, after being folded, is shaped like a trapezoid as viewed from objective optical system 13 and is thus similar in shape to the outer configuration of the prism 33, as shown in FIG. 6. Circuit board 40 is located on the rear side of the prism 33. Accordingly, the outer edge of prism 33 closely overlaps with folded circuit board 40 when seen from the side.

Planar surface 40e with terminals 45 is folded so as to extend inward at the center of the upper shorter side of the trapezoid defined by circuit board 40. The space within this trapezoid is filled with electrically insulating plastic 46. Accordingly, terminals 45 do not extend outside of the confines of the trapezoid defined by circuit board 40. This leads to the reduction of the length and the width of the whole circuit board 40. In case two cables 43 are used, it is advisable to utilize circuit board 40 having two planar surfaces 40e with terminals 45 which can be folded so as to extend inward on both ends thereof, to which lead wires 44 are soldered respectively. Such a circuit board 40 is shown in FIG. 7. The circuit board 40 of FIG. 7 can be folded in a manner similar to that of the circuit board 40 of FIG. 6.

An outer peripheral surface of circuit board 40, after being folded and shaped like a trapezoid, is covered by electrical conducting body 47 along the surface of circuit board 40 so as to form an electrical shielding layer.

Electrical conducting body 47 is also shaped like a trapezoid as viewed from objective optical system 13. Further, an outer surface of electrical conducting body 47 is covered by electrical insulating member 48 in such a manner that an electrical current leakage is prevented from occurring.

Returning to FIG. 2, coupling tube 12 surrounding circuit board 40 is tubular in shape, with the exception of a rear portion thereof (right side in FIG. 2). The distal part of coupling tube 12 is fitted around the body part 11b of distal end body 11. A rear part of coupling tube 12 is fitted into and fixed to foremost nodal ring 2a by means of screws. In order to form holes 51, that have adequate strength in surrounding portions of coupling tube 12, for receiving screws, the inner diameter of the rear end portion of coupling tube 12 is smaller than that of the remaining portion. That is, the thickness of the rear end, in cross section, is larger than that of the remaining portion.

To provide more room inside the endoscope, the rear end portion of coupling tube 12, other than three portions in the proximity, of screw holes 51 formed therein, are machined so as to be cut off, as shown in FIG. 6. As a result, a space large enough to accommodate the respective members to be contained in coupling tube 12 is ensured. Within the portion of the endoscope ranging from bendable portion 1 to coupling tube 12, the available space extends to the circumferential inner surfaces of nodal rings 2, except in the vicinity of the screw holes 51, and allows the respective contained members to be passed therethrough.

In the above-mentioned embodiment of the invention, the rear end portion of coupling tube 12, other than three portions in the proximity of screw holes 51 formed therein, are machined so as to be cut off. However, it is also possible to employ a coupling tube having a rear end portion in which only portions interfering with accommodated respective members to be contained in coupling tube are machined out so as to be cut off.

Instead of the above-mentioned machining, coupling tube 12 may be of a constant thickness and reinforcing material may be added in the vicinity of the screw holes 51. In addition, coupling tube 12 may be coupled with the foremost nodal ring 2 by means of any suitable coupling technique, such as silver brazing and spot welding. Sheathing tube 5 covers the rear part of distal end body 11.

As seen from the foregoing description, in the structure of the distal end portion of the endoscope of the present invention, prism 33 is shaped like a trapezoid in cross section. The trapezoidal shape of prism 33 minimizes the cross sectional area occupied by prism 33 within the distal end body without any degradation of optical performance. Accordingly, the distal end body may be formed in a more slender design and may be easily inserted into a body cavity without unnecessary discomfort for patients.

Further, circuit board 40 is disposed so as to substantially coincide with the shape of prism 33. Thus, the presence of circuit board 40 within distal end body 11 will not increase the diameter of the distal end body 11.

While there has been described what is at the present considered to be the preferred embodiment of the invention, it will be understood by those skilled in the art that various changes and modifications may be made to the disclosed embodiment without departing from the spirit and scope of the invention as defined in the appended claims.

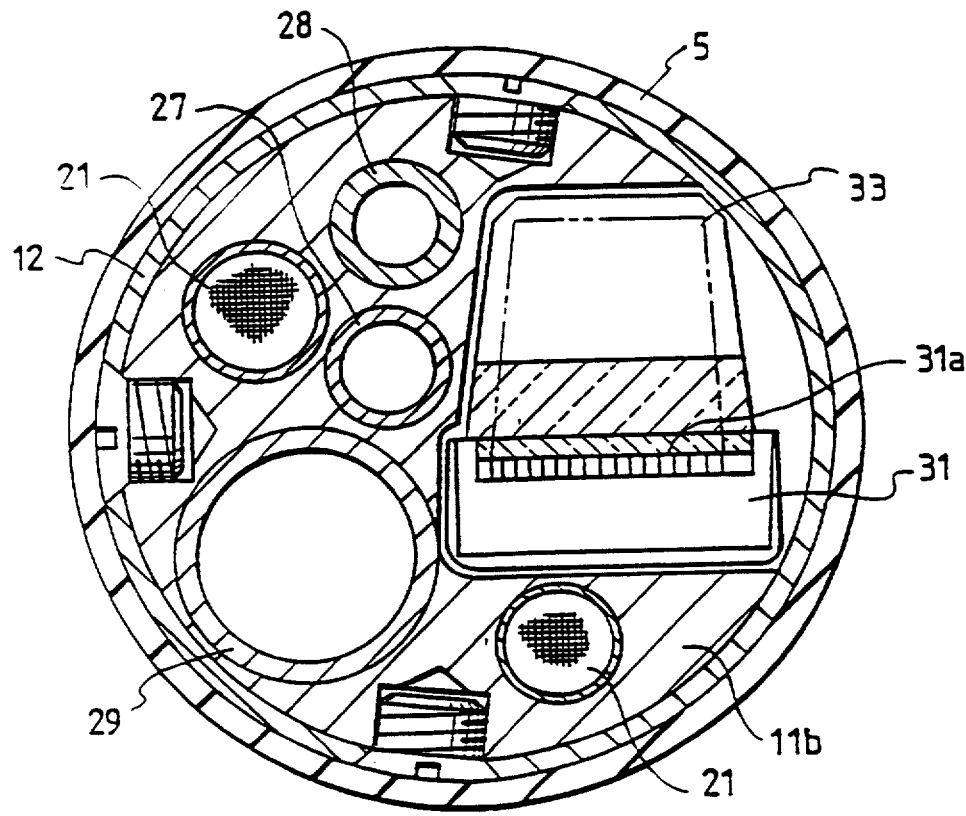

What is claimed is:

1. An electronic endoscope comprising:
   a distal end body;
   an objective optical system disposed within said distal end body and having a center axis;
   a solid state image pickup disposed in said distal end body and having a light receiving surface that is substantially parallel to said center axis; and
   a prism disposed in said distal end body and directing light received from said objective optical system onto said light receiving surface, said prism having a trapezoidal shape in cross section when viewed from said objective optical system, nonparallel sides of said trapezoidal shape being substantially parallel to diverging principle rays of the light travelling through said prism.

2. An endoscope according to claim 1 further comprising:
   a circuit board disposed within said distal end body and coupled to said solid-state image pick-up element, said circuit board being arranged to substantially coincide with the cross-section of said prism when viewed from said objective optical system.

3. An endoscope according to claim 2, wherein said circuit board comprises a plurality of planar surfaces folded so as to form a trapezoid in cross section, a first of said planar surfaces having connection terminals thereon extends toward the interior of said trapezoid.

4. An endoscope according to claim 3, wherein said first planar surface extends inwardly from a center of an upper shorter side of said trapezoid.

5. An endoscope according to claim 2, wherein said circuit board includes terminals formed on both ends thereof, the endoscope further comprising first and second connection cables extending through the endoscope, each of said first and second connection cables having lead wires which are connected to said terminals.

6. An electronic endoscope comprising:
   a distal end body;
   an objective optical system disposed within said distal end body and having a center axis;
   a solid state image pickup disposed in said distal end body and having a light receiving surface that is substantially parallel to said center axis; and
   a prism disposed in said distal end body and directing light received from said objective optical system onto said light receiving surface, said prism having a trapezoidal shape in cross section when viewed from said objective optical system, nonparallel sides of the trapezoidal shape substantially corresponding to diverging principle rays of the light travelling through said prism.

* * * * *

UNITED STATES PATENT AND TRADEMARK OFFICE
CERTIFICATE OF CORRECTION

PATENT NO. : 5,427,087  
DATED : June 27, 1995  
INVENTOR(S) : Ito, et al

It is certified that error appears in the above-indentified patent and that said Letters Patent is hereby corrected as shown below:

The title page should be deleted to be replaced with the attached title page.

Signed and Sealed this

Seventeenth Day of October, 1995

Attest:

BRUCE LEHMAN

*Attesting Officer*  *Commissioner of Patents and Trademarks*

United States Patent [19]
Ito et al.

[11] Patent Number: 5,427,087
[45] Date of Patent: Jun. 27, 1995

[54] STRUCTURE OF THE DISTAL END PORTION OF AN ENDOSCOPE

[75] Inventors: Keiji Ito; Hiroshi Iwata, both of Tokyo, Japan

[73] Assignee: Asahi Kogaku Kogyo Kabushiki Kaisha, Tokyo, Japan

[21] Appl. No.: 797,975

[22] Filed: Nov. 26, 1991

[30] Foreign Application Priority Data

Nov. 26, 1990 [JP] Japan ................. 2-321418

[51] Int. Cl.$^6$ ................................................. A61B 1/04
[52] U.S. Cl. ..................................... 128/4; 128/6
[58] Field of Search ................... 128/4, 6, 7, 8, 11, 128/13; 358/98; 385/36, 116, 117, 119; 359/831, 833, 836

[56] References Cited

U.S. PATENT DOCUMENTS

| | | |
|---|---|---|
| 4,741,327 | 5/1988 | Yabe ........................ 128/6 |
| 4,832,003 | 5/1989 | Yabe ........................ 128/6 |
| 4,895,138 | 1/1990 | Yabe ........................ 128/6 |

Primary Examiner—Richard J. Apley
Assistant Examiner—John P. Leubecker
Attorney, Agent, or Firm—Sughrue, Mion, Zinn, Macpeak & Seas

[57] ABSTRACT

The distal end body of an endoscope accommodates an objective optical system, and a solid-state image pick-up element having a light receiving surface is disposed axially in parallel with the center axis of the objective optical system. A prism is disposed such that the optical axis of the objective optical system is perpendicular to the center axis of the light receiving surface. An object is imaged on the light receiving surface of the solid-state image pick-up element, through the objective optical system. The prism is shaped like a trapezoid in cross-section to minimize the size of the endoscope.

6 Claims, 5 Drawing Sheets